US008580931B2

(12) United States Patent
Kumpalume et al.

(10) Patent No.: US 8,580,931 B2
(45) Date of Patent: Nov. 12, 2013

(54) METHOD FOR THE PURIFICATION OF ALPHA-1-ANTITRYPSIN

(75) Inventors: Peter Kumpalume, Watford (GB); Adrian Podmore, Alconbury (GB); Joan Dalton, Elstree (GB)

(73) Assignee: Bio Products Laboratory Limited, Hertfordshire (GB)

( * ) Notice: Subject to any disclaimer, the term of this patent is extended or adjusted under 35 U.S.C. 154(b) by 733 days.

(21) Appl. No.: 12/095,488

(22) PCT Filed: Nov. 29, 2006

(86) PCT No.: PCT/GB2006/004458
§ 371 (c)(1),
(2), (4) Date: Jan. 16, 2009

(87) PCT Pub. No.: WO2007/063299
PCT Pub. Date: Jun. 7, 2007

(65) Prior Publication Data
US 2009/0292114 A1    Nov. 26, 2009

(30) Foreign Application Priority Data

Nov. 30, 2005   (GB) .................................. 0524432.2

(51) Int. Cl.
*C07K 1/00* (2006.01)
*A23J 1/00* (2006.01)
(52) U.S. Cl.
USPC .......................................... 530/395; 530/412
(58) Field of Classification Search
None
See application file for complete search history.

(56) References Cited

U.S. PATENT DOCUMENTS

| 4,379,087 A | 4/1983 | Coan et al. |
| 4,439,358 A | 3/1984 | Coan et al. |
| 4,629,567 A | 12/1986 | Bollen et al. |
| 4,656,254 A | 4/1987 | Shearer et al. |
| 4,697,003 A | 9/1987 | Coan |
| 5,616,693 A * | 4/1997 | Hwang et al. ............... 530/392 |
| 6,525,176 B1 * | 2/2003 | Lee et al. ................... 530/350 |
| 2002/0082214 A1 | 6/2002 | Mattes et al. |
| 2004/0124143 A1 | 7/2004 | Kee et al. |

FOREIGN PATENT DOCUMENTS

| DE | 44 07837 C1 | 8/1995 |
| EP | 0067293 A2 | 12/1982 |
| EP | 0282363 A2 | 9/1988 |
| WO | WO 95/35306 A1 | 12/1995 |
| WO | WO 97/09350 A1 | 3/1997 |
| WO | WO 98/00154 A1 | 1/1998 |
| WO | WO 02/060952 A1 | 8/2002 |
| WO | WO 2005/027821 A2 | 3/2005 |

OTHER PUBLICATIONS

SAFC Biosciences Technical Bulletin (Apr. 2006).*
The Basics of Chromatography (Jul. 2003) in bioPharm Internationla Guide.*

(Continued)

*Primary Examiner* — Alexander Kim
(74) *Attorney, Agent, or Firm* — Knobbe, Martens, Olson & Bear, LLP

(57) ABSTRACT

The invention relates to methods for the isolation of AAT from solutions containing albumin and AAT using at least two separate metal chelate chromatography steps. The product may be further purified and/or subjected to one or more virus inactivation or reduction steps. The isolated AAT may then be formulated for pharmaceutical use.

19 Claims, 4 Drawing Sheets

(56) References Cited

OTHER PUBLICATIONS

Smith et al. (1990) ACS Symposium Series; American Chemical Society; Washington DC; pp. 168-180.*

Kagedal, Protein Purification: Principles, High-Resolution Methods, and Applications, Second Edition, 1998, Wiley-VCH, Inc.*

Bonsdorff et al., Development of a Pharmaceutical Apotransferrin Product for Iron Binding Therapy, Biologicals, 2001, vol. 29, pp. 27-37.*

Vellekamp et al., Empty Capsids in Column-Purified Recombinant Adenovirus Preparations, Human Gene therapy, (2001), vol. 12, pp. 1923-1936.*

Von Jagow et al. A Practical Guide to Membrane Protein Purification, (1994) Elsevier Science (USA), p. 40; which discloses "Flow-through Mode" in protein purification.*

Cohn, E.J. et al. 1946 "Preparation and properties of serum and plasma proteins. IV. A system for the separation into fractions of the proteins and lipoprotein components of biological tissues and fluids" *J Am Chem Soc* 68:459-475.

Dubin, A. et al. 1990 "Isolation of nine human plasma proteinase inhibitors by sequential affinity chromatography" *Prep Biochem* 20:63-74.

Fujita, J. et al. 1999 "Modulation of elastase binding to elastin by human alveolar macrophage-derived lipids" *Am J Respir Crit Care Med* 160: 802-807.

Jain, S. and Gupta, M.N. 2005 "An integrated process for separation of major and minor proteins from goat serum" *App Biochem Biotech* 125:55-62.

Kistler, P and Nitschmann, Hs. 1962 "Large scale production of human plasma fractions" *Vox Sang* 7:414-424.

Kurecki, T. et al. 1979 "Purification of human plasma $\alpha 2$ macroglobulin and $\alpha 1$ proteinase inhibitor using zinc chelate chromatography" *Anal.Biochem* 99:415-420.

Porath, J. et al. 1975 "Metal chelate affinity chromatography, a new approach to protein fractionation" *Nature* 258:598-599.

* cited by examiner

METHOD FOR THE PURIFICATION OF ALPHA-1-ANTITRYPSIN

This application is U.S. National Phase of International Application PCT/GB2006/004458, filed Nov. 29, 2006, designating the U.S., and published in English as WO 2007/063299 on Jun. 7, 2007, which claims priority to United Kingdom Patent Application No. 0524432.2, filed Nov. 30, 2005.

The present invention concerns methods for the purification of alpha-1-antitrypsin.

Alpha-1-antitrypsin (AAT), also known as alpha-1-protease inhibitor, is an essential protease inhibitor found mainly in the blood. AAT normally protects connective tissue, such as the elastic tissues of the lungs, from degradation by elastase, an enzyme released by neutrophils at sites of inflammation.

Hereditary emphysema is a disease that results from a genetic deficiency of AAT. Hereditary emphysema may affect both the structure and the function of the lungs and can lead to chronic emphysema and premature death if left untreated. Unopposed elastolysis is thought to be the mechanism by which emphysema develops in these individuals and hence intravenous administration of purified AAT is a standard treatment for AAT deficiency. Cystic fibrosis is another pathology in which a chronic imbalance of elastase and AAT results in tissue damage. AAT treatment is used to counteract this imbalance and prevent tissue damage.

Early attempts to purify large quantities of AAT from plasma focused on using side fractions from cold ethanol fractionation processes. Cohn fraction IV-1 precipitate, a waste fraction in the manufacture of albumin, has been the most frequently selected.

EP-A 0067293 describes a method of purifying AAT from Cohn fraction IV-1 in which the proteins of the Cohn fraction IV-1 precipitate are destabilised by exposure to reducing agents which break disulphide bonds. The destabilised proteins are then precipitated (salted out) using high salt concentrations. Since AAT is not stabilised by disulphide bonds it is not destabilised by the reducing agents and can therefore be recovered from the supernatant by chromatography.

U.S. Pat. Nos. 4,379,087 and 4,439,358 used more conventional methods to isolate AAT from Cohn fraction IV-1. In the methods of these patents, PEG is used to remove high molecular weight and denatured impurities from the starting material by precipitation. This is followed by anion exchange chromatography to reduce albumin and other lower molecular weight contaminants. However, yields were extremely low with these methods. U.S. Pat. No. 4,656,254 suggests that the methods of U.S. Pat. Nos. 4,379,087 and 4,439,358 could achieve a final container yield of only 4 to 6% when pooled plasma was used. U.S. Pat. No. 4,656,254 discloses that increased yields of up to 500 fold can be achieved by increasing the volume of the Cohn fraction IV-1 sample by 24 volumes and increasing the pH to between pH 9-10 prior to performing the methods described in U.S. Pat. Nos. 4,379,087 and 4,439,358.

Other methods, such as those of WO2005/027821, have been shown to achieve a product of higher purity from Cohn fraction IV-1. The method of WO2005/027821 uses a precipitation step followed by a stepwise chromatography cascade of anion exchange, cation exchange and a second anion exchange.

The limitations of Cohn fraction IV-1 as a source of AAT have been recognised and alternative Cohn fractions such as Cohn fraction II & III supernatant (also known as supernatant A in the modified Cohn fractionation method described by Kistler and Nitschmann, 1962, Vox Sang, 7, p 414 to 424) have been used. According to the literature, Cohn fraction II & III supernatant contains 2 or 3 times more active AAT than Cohn fraction IV-1.

A+1 Supernatant may be prepared as shown in FIG. 4. However, purifying AAT from A+1 supernatant has its own disadvantages compared to using Cohn fraction IV-1. Firstly, it contains huge quantities of albumin that must be removed from the processing stream. Secondly, this albumin is an essential product in its own right, and hence any commercially useful process must also allow for co-purification of the albumin. Thus, only methods that do not destroy the tertiary structure of albumin should be employed. To be commercially useful, any method for AAT purification that uses A+1 supernatant as the starting material must be able to provide economic production of albumin and AAT, and potentially also other plasma proteins of interest.

U.S. Pat. No. 4,697,003 and EP-A 0282363 remove ethanol from supernatant A by diafiltration or gel filtration. However, removal of the ethanol in supernatant A by diafiltration or gel filtration becomes expensive and time consuming when large volumes of starting material are used. After removal of ethanol, both albumin and AAT are subjected to anion exchange chromatography in which both AAT and albumin are bound to the solid support. In EP-A 0282363 the purity of AAT is improved by eluting albumin first, then increasing sodium acetate levels in order to elute AAT. In U.S. Pat. No. 4,697,003, AAT is eluted without first eluting albumin. The methods of both U.S. Pat. No. 4,697,003 and EP-A 0282363 describe further purification steps following the anion exchange chromatography step. EP-A 0282363 describes gel filtration whilst U.S. Pat. No. 4,697,003 uses PEG precipitation. The method of EP-A 0282363 achieves 80-90% purity and a 65-75% yield. This is equivalent to a 50-60% recovery of plasma AAT.

It is the aim of the present invention to improve what is currently available for the isolation of AAT in one or more of the following respects: yield and/or purity of AAT and reproducibility thereof, simplicity of process and suitability for use on a large and/or commercial scale or to at least provide an alternative method for the isolation of AAT.

It has now been found that AAT can be isolated from a solution containing albumin and AAT using at least two separate metal chelate chromatography steps. This simple method results in high, reproducible yields of AAT, is capable of economic use on a large scale, and can provide AAT which is sufficiently pure for therapeutic applications. Metal chelate chromatography is also known as immobilised metal ion affinity chromatography (IMAC).

The use of metal chelate chromatography (IMAC) for fractionating plasma proteins was originally described by Porath (Porath, J et al., Nature 258:598-599 (1975)). Kurecki (Kurecki, T. et al., Anal. Biochem. 99:415-420 (1979)), used a Zn chelate for the purification of alpha 2 macroglobulin and AAT from an ammonium sulphate fraction of plasma, but the AAT needed further purification by anion exchange chromatography. In WO95/35306, a Cu or Zn chelate was used as a polishing step, subsequent to PEG precipitation and anion exchange chromatography. In WO97/09350, a Ni chelate was used as the fifth stage in a multistep process to purify AAT from transgenic sheep milk. Unlike these prior art methods, in the present invention metal chelate chromatography is used as a major purification step, allowing a simple, scaleable process for the large scale purification of AAT.

In one aspect the present invention therefore provides a first method for the isolation of alpha-1-antitrypsin (AAT) from a solution containing albumin and AAT, comprising the steps of:

(a) loading the solution onto a first metal chelate chromatography substrate under conditions whereby AAT is retained on the substrate and albumin is not;

(b) washing the substrate to remove unbound or weakly bound proteins and then selectively eluting AAT from the substrate;

(c) loading the AAT eluate obtained from step (b) onto a second metal chelate chromatography substrate under conditions whereby AAT remains in solution and is not retained on the substrate;

(d) collecting the AAT solution from step (c); and (e) optionally carrying out one or more further chromatographic purification steps on the AAT solution, for example an anion exchange chromatography step.

In the first method, an additional chromatographic purification step may also optionally be present between steps (b) and (c). For example, an anion exchange chromatography step may be present. However, preferably step (c) follows directly after step (b).

In another aspect, the invention provides a second method for the isolation of alpha-1-antitrypsin (AAT) from a solution containing albumin and AAT, comprising the steps of:

(a1) removing albumin from the solution;

(b1) loading the albumin depleted solution onto a first metal chelate chromatography substrate under conditions whereby AAT remains in solution and is not retained on the substrate;

(c1) collecting the solution containing AAT;

(d1) loading the solution obtained from step (c1) onto a second metal chelate chromatography substrate under conditions whereby AAT is retained on the substrate; and (e1) selectively eluting AAT from the second substrate.

Although the above order of steps in the second method is preferred, the order of the steps may be interchanged such that steps (d) and (e) are before steps (b) and (c). Thus, the present invention also provides a third method for the isolation of alpha-1-antitrypsin (AAT) from a solution containing albumin and AAT, comprising the steps of:

(a2) removing albumin from the solution;

(b2) loading the albumin depleted solution onto a first metal chelate chromatography substrate under conditions whereby AAT is retained on the substrate;

(c2) selectively eluting AAT from the substrate;

(d2) loading the solution obtained from step (c2) onto a second metal chelate chromatography substrate under conditions whereby AAT remains in solution and is not retained on the substrate; and (e2) collecting the solution containing AAT.

By "isolation" it is meant that preferably at least 50% of AAT present in the starting sample is present in the product of the methods of the invention. Preferably at least 65% and most preferably at least 80% of AAT present in the starting sample is present in the product. The AAT obtained using the methods of the invention will preferably be at least 70% pure, more preferably at least 80% pure and most preferably 90% pure. The AAT obtained using the methods of the invention will preferably be at least 75% active, more preferably at least 85% active and most preferably 95% active, as measured by for example elastase binding activity. It should be noted that, like all isolation procedures, increases in purity are often associated with decreases in yield. Also stages added to ensure viral safety may lower the overall recovery.

The skilled man will be aware of techniques by which the purity, yield and/or activity of an AAT isolate of the invention can be determined. For example, purity can be determined by SDS polyacrylamide gel electrophoresis (SDS-PAGE). Activity can be determined by an elastase inhibition assay (Fujita et al., Am. J. Respir. Crit. Care Med., v160, no. 3, September 1999, 802-807). Yield can be determined by comparing the total activity of the final product with the total activity of the starting material.

Preferably, the "solution containing albumin and AAT" is plasma, or a plasma fraction. By "plasma fraction" it is meant a solution which has been obtained by fractionating plasma. Common plasma fractionation processes are the Cohn fractionation method (Cohn et al, 1946, J Am Chem Soc, 68: 459) and its modifications (e.g. Kistler and Nitschmann, 1962, Vox Sang, 7: 414-424). This process begins with cryoprecipitation to remove some of the coagulation factors. The resultant cryoprecipitate-depleted plasma pool is treated to precipitate IgG fraction (Fraction 1 according to the Kistler and Nitschmann method at 19% ethanol, pH 5.85 and $-5°$ C.; or the equivalent Fraction II+III according to the Cohn method at 25% ethanol, pH 6.9 and $-5°$ C.). The remaining impurities are removed by precipitation of Fraction IV at 40% ethanol at pH 5.85 and $-5°$ C. according to the Kistler and Nitschmann method or a two step process according to Cohn (Fr IV-I at 18% ethanol, pH 5.2, $-5°$ C. followed by Fr IV-4 at 40% ethanol, pH 5.8, $-5°$ C.). Lowering the pH of the fraction IV supernatant to 4.8 and then dropping the temperature from $-5°$ C. ($\pm 1°$ C.) to $-10°$ C. ($\pm 3°$ C.) while maintaining the ethanol concentration at 40% causes the precipitation of Cohn fraction V. Any of the fractions obtained in the above mentioned fractionation processes which contain both albumin and AAT are of use as starting materials for the methods of the present invention.

The supernatant of the Kistler and Nitschmann fraction A+1 is particularly suitable for use as the starting material in the present invention. The A+1 supernatant is derived from plasma from which fibrinogen, coagulation factors and immunoglobulins have been removed, and comprises mainly AAT, alpha-1-acid glycoprotein (AAG), transferrin, haptoglobin (Hp), alpha-2 HS glycoprotein, haemopexin, alpha-2 macroglobulin, alpha-1 antichymotrypsin and albumin. It is prepared by a modification of the Kistler and Nitschmann method in which the starting plasma is treated with Celite followed by fractionation at 19% ethanol, pH 5.85 at $-5°$ C., leading to a combination of Fraction 1 with Supernatant A of the Kistler and Nitschmann method. Any fractions equivalent in terms of composition to the above-mentioned fractions obtained in an alternative manner or known by an alternative terminology are considered to be suitable starting materials for the methods of the invention. Any sub-fractions of the above-mentioned fractions which comprise AAT and albumin are also of use as starting materials.

By "plasma fraction" it is also meant any solution containing albumin and AAT obtained by removing one or more plasma components from plasma. The method of removing the plasma component is immaterial and may for example be affinity chromatography, anion exchange chromatography, size exclusion chromatography or precipitation methods. The components removed will preferably be immunoglobulins, coagulation factors such as Factor VIII and/or fibrinogen. The skilled man would be able to remove these and other plasma components from plasma without undue burden.

The plasma used in the methods of the invention and the plasma used for fractionation or for obtaining plasma fractions may be from any suitable source although plasma from mammalian blood is preferred. Most preferred is plasma from human blood. Accordingly, the AAT purified by the methods of the invention is preferably mammalian AAT and most preferably human AAT. However, the AAT purified by the methods of the invention might be AAT from a species that is different from the species from which the solution containing albumin and AAT has been derived. In other words, exogenous AAT artificially expressed in a host (e.g. a transgenic animal) can be purified from solutions containing albumin and AAT derived from that host. Conveniently the host will be an mammalian animal that is transgenic for AAT from a species of interest (e.g. human AAT) and the AAT transgene expression product is found in one or more of the body fluids of that animal that contain albumin. Preferably the body fluid containing the AAT transgene expression product is the plasma of the animal.

Preferably, the majority of proteinaceous components present in the starting material will be proteinaceous components derived from plasma or a plasma fraction. Preferably the only proteinaceous components will be those derived from plasma or a plasma fraction.

If necessary, the pH of the starting solution should be adjusted such that no undue damage to the AAT occurs before it is purified according to the methods of the invention. A pH range of between 5 and 7 is preferred. More preferred is a pH of between 5.5 and 6.5 and most preferable is a pH of about 6.2. AAT also tends to denature if left in contact with high concentrations of ethanol for any length of time. If high concentrations of ethanol are present in a plasma fraction, then it may be necessary to dilute the fraction using a suitable buffer to lower the ethanol concentrations and hence preserve AAT activity before carrying out the methods of the invention. The fact that AAT is unstable in ethanol is well known from the literature. For example, a 20% ethanol concentration will inactivate as much as 75% of the AAT present within two weeks.

Metal chelate chromatography substrates comprise metal ions chelated to ligands which are attached to a solid support. The most commonly used substrates utilise divalent transition metal ions such as zinc ($Zn^{2+}$), nickel ($Ni^{2+}$) or copper ($Cu^{2+}$) to form stable complexes with histidine, tryptophan and cysteine residues within the proteins to be purified. Cadmium, mercury, calcium, cobalt or $Fe^{2+}$ ions can also be used. Affinity is not specific to the amino acid sequence of the protein, but metal chelate chromatography can preferentially isolate metal-ion-binding proteins. Once bound, the proteins can be selectively eluted by controlling pH or using competitor molecules such as imidazole or amino acids in the elution buffers.

A preferred metal chelate chromatography substrate for use in the present invention comprises nitrilotriacetic acid (NTA) as the chelating ligand, for example linked to agarose as the solid support. A suitable product with nickel as the metal ion is available under the trade name HisTrap Sepharose® (Amersham Biosciences). The nickel can be replaced with another cation by stripping and reloading the substrate following the manufacturer's instructions. Another preferred metal chelate chromatography substrate comprises iminodiacetic acid as the chelating ligand, for example linked to agarose as the solid support. A suitable product is available under the trade name Chelating Sepharose® (Amersham Biosciences). Chelating Sepharose® may be charged with any suitable metal ion.

The metal chelate affinity chromatography substrates of use in the present invention are charged with divalent transition metal cations or divalent calcium cations, preferably $Zn^{2+}$, $Ni^{2+}$, $Cu^{2+}$, $Co^{2+}$, or $Fe^{2+}$, more preferably $Ni^{2+}$, $Cu^{2+}$ or $Zn^{2+}$ and most preferably $Cu^{2+}$. The skilled man would be able to choose suitable metal ions and accompanying conditions to achieve the necessary binding profiles. Different metal cations may be used on each of the two metal affinity chromatography substrates used in the methods of the invention, but preferably the same cation will be used to minimise the number of possible sources of metal ion contamination in the final product.

A preferred substrate to allow binding of AAT and flow through of albumin is chelating Sepharose (agarose) charged with $Cu^{2+}$ ions. A preferred substrate to allow AAT to flow through is NTA agarose charged with $Cu^{2+}$ ions.

Thus in preferred embodiments of the methods of the invention, the metal chelate chromatography substrate used in step (c), step (b1) or step (d2) is NTA agarose, preferably charged with $Cu^{2+}$ ions, and the substrate used in step (a), step (d1) or step (b2) is a chelating Sepharose (agarose) substrate, preferably charged with $Cu^{2+}$ ions.

Step (a) of the first method should also remove any ethanol in the starting solution, as the ethanol will not bind to the metal chelate chromatography substrate.

Removal of albumin in step (a1) or step (a2) can be achieved by any convenient means. Preferably, substantially all the albumin is removed, for example at least 90% of the albumin (as determined by Bradford assay and densitometry estimations on SDS-PAGE). If A+1 supernatant is used as the starting material, the major component will normally be albumin (for example, approximately 90% of the total protein will be albumin). The skilled man would be aware of suitable means for the removal of albumin, although affinity chromatography, ion exchange chromatography, metal chelate chromatography, specific degradation techniques, or precipitation techniques are mentioned as examples. Anion exchange chromatography is preferred.

Anion exchange chromatography commonly uses substrates such as, but not limited to, dextran, cellulose and modifications thereof that are positively charged. These substrates can comprise part of the solid support (e.g. a coating) or can form the entirety of the solid support. The solid support may be in particulate form (e.g. a resin) however non-particulate supports (e.g. filter papers or gels) may be used. Particulate substrates are typically, though not always, packed into columns.

When the term "substrate" is used herein it should be interpreted as referring to substrates in a form suitable for use in relevant chromatography step, for example an anion exchange or metal chelate chromatography step as appropriate for the context the term is used in. For ease of processing, the different chromatography substrates used in the methods of the invention are preferably packed into columns.

A sample which is to undergo anion exchange chromatography is applied to the anion exchange substrate. On the basis of charge interactions, (negatively charged) molecules within the sample bind to the substrate. Washing of the substrate therefore removes unbound or weakly bound molecules. Controlled/selective elution of the bound molecules can be achieved by passing solutions of increasing salt concentration over the substrate since this disrupts the charge interactions between the substrate and the bound molecules. The pH of the elution solution may also be altered to induce elution, since this will alter the charge present on the bound molecule and the substrate. The weaker the charge interaction between the molecule and the substrate, the lower the concentration of salt required to disrupt the interaction and thus induce the elution of that molecule from the substrate. By carefully controlling salt concentration, selective elution of bound molecules can be achieved.

The strength of the charge interaction can be modified by the choice of material for the solid support. For instance QAE-Sephadex® or GE cellulose are strong anion exchanger substrates and DEAE-cellulose and DEAE-Sephadex® are weak anion exchange substrates.

The skilled person will be well aware of anion exchange techniques and tools and would be able to devise and perform an anion exchange protocol that would remove substantially all the albumin from the sample in step (a1) or step (a2). Conveniently the substrate and the conditions will be selected such that albumin will flow through the substrate and AAT will be retained and then selectively eluted. This is advantageous when the starting material contains larger amounts of albumin than AAT, which will be the case if the starting material is the A+1 supernatant. If the conditions are selected such that the albumin flows through the substrate, a smaller volume of substrate is required than would be required if all the albumin was to bind to the substrate.

Thus in a preferred embodiment, step (a1) in the second method of the invention, or step (a2) in the third method of the invention, comprises loading the solution containing albumin and AAT onto an anion exchange substrate under conditions whereby AAT is retained on the substrate and most of the albumin is not; washing the substrate to remove unbound albumin and then selectively eluting the AAT from the substrate. Any ethanol present in the starting solution will also be removed, as it will not be retained by the anion exchange substrate and hence can be washed off.

Of particular utility as the anion exchange substrate in step (a1) or step (a2) is quaternary amino linked agarose, for example quaternary amino linked Sepharose® (Amersham Biosciences), in particular the substrate marketed under the name Capto Q® (Amersham Biosciences). Capto Q® is a high capacity strong quaternary ammonium (Q) anion exchanger coupled to a chemically modified (dextran coated), high-flow agarose matrix. The quaternary amino group in Capto Q is $-N^+(CH_3)_3$. Sepharose® is the commonly used trade name for agarose beads. Other suitable anion exchange substrates include cellulose, dextran and polymer based beads.

An advantage of using anion exchange chromatography in step (a1) or step (a2) is that any AAG present in the starting material will tend to bind to the anion exchange substrate more strongly than does AAT. Therefore, AAT may be selectively eluted from the substrate leaving any AAG bound. If desired, the AAG can then be selectively eluted after the AAT.

The first method of the invention may further comprise an anion exchange chromatography step performed under conditions whereby AAT is bound by the anion exchange substrate and is subsequently selectively eluted therefrom. This additional step may conveniently be performed before or after steps (c) and (d). The discussion of anion exchange chromatography above applies *mutatis mutandis* to this aspect of the invention. Alternatively, other known chromatographic purification steps may be performed before or after steps (c) and (d).

The following discussion is applicable to all the methods of the inventions unless otherwise indicated.

It is envisaged that the methods of the invention may comprise one or more additional steps. For instance, one or more washing steps may be employed in the steps in which AAT is retained on the chromatography substrate to reduce unwanted molecules in the AAT eluate. The object of a washing step is to pass a suitable buffer across the substrate which will elute unbound, or very weakly bound, molecules of the sample (e.g. albumin) without inducing the elution of the target molecule (AAT). Most commonly, one or more washing steps will be included between the step of loading the sample onto the chromatography substrate and the step of selectively eluting AAT therefrom. However, washing steps may be included inbetween distinct elution steps, especially if other potentially useful molecules are to be eluted prior to the elution of AAT.

The skilled man will be aware of suitable loading, washing and elution buffers and will be able to formulate suitable buffers (in terms of constituents and their concentrations and pH) to achieve either loading onto, washing of AAT (or other molecules of interest) bound to, or selective elution of AAT (or other molecules of interest) from the particular chromatography substrate being used. The skilled man will be able to optimise these parameters without undue burden. The loading, washing and elution conditions should be selected such that no unnecessary damage to the AAT occurs. Typical loading, washing and elution buffers comprise a phosphate component and a salt. Suitable phosphate components include, but are not limited to, $NaH_2PO_4$, $Na_2HPO_4$, $KH_2PO_4$ and $K_2HPO_4$. A preferred buffer component is a mixture of $Na_2HPO_4$ and $NaH_2PO_4$. Suitable salts include sodium chloride, potassium chloride, and sodium sulphate. A preferred salt is sodium chloride.

Depending on the other constituents present in the solution which bind to the chromatography substrate, it may be necessary to carry out step-wise elution to obtain AAT with a high degree of purity. Contaminants which bind to the substrate less strongly than AAT can be eluted first by suitable choice of initial elution conditions. Similarly, the elution buffer used to elute the AAT should be chosen such that it does not remove contaminants which bind to the substrate more strongly than does AAT. For example, AAG binds to anion exchange substrates such as Capto Q® Sepharose® more strongly than does AAT, and AAG may remain bound to the column after AAT is eluted. If desired, an elution buffer of greater salt concentration than that used to elute AAT can be used to elute AAG after the AAT has been eluted.

Washing and elution conditions for the metal chelate chromatography steps may also use competitor compounds such as amino acids or imidazole. By optimising the concentration of the competitor compound in an elution buffer, selective elution of substances bound to the chromatography substrate can be achieved. For example, haptoglobin and transferrin bind to $Cu^{2+}$ charged NTA linked agarose more strongly than does AAT and may remain bound to the substrate after AAT is eluted. An elution buffer of greater imidazole concentration than that used to elute AAT can be used to elute Hp and transferrin. Similarly, the concentration of a competitor molecule in a loading buffer may be optimised to prevent binding of AAT to the metal chelate chromatography substrate thus ensuring its effective flow through when required.

The skilled man will be aware of techniques for monitoring the eluate to enable the progress of the elution to be followed and to ascertain what is being eluted in the various fractions. For instance, UV spectroscopy can follow the progress of elution in real time. Techniques such as HPLC SEC or SDS PAGE can be used to detect the presence and identity of impurities. Matrix assisted laser desorption ionization time-of-flight (MALDI-ToF) mass spectrometry of HPLC fractions or SDS-PAGE bands can also be used to identify the proteins present. Known proteins can be monitored with antibody-based detection methods (e.g. enzyme-linked immunosorbent assay (ELISA), radial immuno diffusion (RID) and tubimetric determinations).

Loading and washing buffers are often the same in terms of buffer constituents and the amounts thereof. However, the skilled man will be capable of devising separate loading and washing buffers from his common general knowledge should it be necessary.

Preferably all buffers used in a single method of the invention will use an identical buffer component and an identical type of salt, albeit in different concentrations to meet the various functional requirements of each buffer. This minimises the number of potential contaminants in the product AAT arising from the process. Most preferably all the buffers of use in the invention will comprise a phosphate buffer component and sodium chloride.

The conductivity of the loading and washing buffers is preferably less than 7 mS/cm, more preferably less than 6 mS/cm and most preferably less than 5.0 mS/cm. The conductivity is preferably between 4.5 and 5 mS/cm to ensure that most of the albumin flows through but the AAT still binds to any anion exchange matrix used. The conductivity should not affect binding onto metal chelate columns (for example, up to 1M NaCl (conductivity ~80 mS/cm) is a recommended additive in metal chelate chromatography to prevent non specific interactions).

The pH of the loading, washing and elution buffers is also important. The pH of the buffers should be maintained at a level that does not substantially damage AAT. The pH should also be selected carefully because pH may effect the conductivity of the buffer depending on the buffer constituents used and may also induce the elution or retention (desired or not) of the target molecule from the substrate. A pH range of between 5 and 7 is preferred. More preferred is a pH of between 5.5 and 6.5 and most preferable is a pH of about 6.2. The skilled man will be aware of the relationship between pH and degree of elution and retention, and will be able to select precise pH ranges which are appropriate for the buffers and substrates being used and the function they are performing. Common general knowledge will enable optimisation of buffer parameters without undue burden As mentioned above, a preferred anion exchange substrate is quaternary amino linked agarose. Binding of AAT to this substrate and flow through of albumin can be achieved with a buffer comprising a phosphate buffer component and sodium chloride wherein the buffer component is between 10 and 30 mM, preferably between 15 and 25 mM, most preferably about 20 mM; the sodium chloride is between 20 and 40 mM, preferably between 25 and 35 mM and most preferably about 30 mM; and the pH is between 5 and 7, preferably between 6 and 6.5, most preferably about 6.2.

Elution of AAT from quaternary amino linked agarose can be achieved with a buffer comprising a phosphate buffer component and sodium chloride wherein the buffer component is between 10 and 30 mM, preferably between 15 and 25 mM, most preferably about 20 mM; the sodium chloride is between 140 and 200 mM, preferably between 155 and 185 mM and most preferably about 170 mM; and the pH is between 5 and 7, preferably between 6 and 6.5, most preferably about 6.2.

Elution of AAG from quaternary amino linked agarose can be achieved with a buffer comprising a phosphate buffer component and sodium chloride wherein the buffer component is between 10 and 30 mM, preferably between 15 and 25 mM, most preferably about 20 mM; the sodium chloride is between 400 and 600 mM, preferably between 450 and 550 mM and most preferably about 500 mM; and the pH is between 5 and 7, preferably between 6 and 6.5, most preferably about 6.2.

Flow through of AAT and retention of haptoglobin and transferrin on $Cu^{2+}$ charged NTA linked agarose can be achieved with a buffer comprising a phosphate buffer component, sodium chloride and imidazole wherein the buffer component is between 10 and 30 mM, preferably 15 and 25 mM, most preferably about 20 mM; the sodium chloride is between 20 and 40 mM, preferably between 25 and 35 mM and most preferably about 30 mM, the imidazole is between 1.5 and 3.5 mM, preferably 2 and 3 mM and most preferably about 2.5 mM; and the pH is between 5 and 7, preferably between 6 and 6.5, most preferably about 6.2. The concentration of imidazole or other competitor molecules, if used, should be carefully selected to ensure it is sufficient to prevent AAT binding but not to prevent haptoglobin or transferrin binding. The affinity of imidazole to a metal ion depends on its concentration. Thus, by carefully choosing the right concentration, Hp will have a greater affinity for the metal chelate chromatography substrate than does imidazole, which in turn will have a greater affinity for the substrate than does AAT.

Elution of haptoglobin and transferrin from $Cu^{2+}$ charged NTA linked agarose can be achieved with a buffer comprising a phosphate buffer component and sodium chloride wherein the buffer component is between 10 and 30 mM, preferably 15 and 25 mM, most preferably about 20 mM; the sodium chloride is between 20 and 40 mM, preferably between 25 and 35 mM and most preferably about 30 mM, the imidazole is between 15 and 25 mM, preferably 17 and 23 mM and most preferably about 20 mM; and the pH is between 7 and 9, preferably between 7.5 and 8.5, most preferably about 8

Flow through of albumin and retention of AAT on $Cu^{2+}$ charged iminodiacetic acid linked agarose can be achieved with a buffer comprising a phosphate buffer component, sodium chloride and imidazole wherein the buffer component is between 10 and 30 mM, preferably 15 and 25 mM, most preferably about 20 mM; the sodium chloride is between 20 and 40 mM, preferably 25 and 35 mM and most preferably about 30 mM; the imidazole is between 1.5 and 3.5 mM, preferably 2 and 3 mM and most preferably about 2.5 mM; and the pH is between 5 and 7, preferably between 6 and 6.5, most preferably about 6.2.

Elution of AAT from $Cu^{2+}$ charged iminodiacetic acid linked agarose can be achieved with a buffer comprising a phosphate buffer component, sodium chloride and imidazole wherein the buffer component is between 10 and 30 mM, preferably 15 and 25 mM, most preferably about 20 mM; the sodium chloride is between 20 and 40 mM, preferably between 25 and 35 mM and most preferably about 30 mM; the imidazole is between 2.5 and 20 mM, preferably 2.5 and 15 mM and most preferably 2.5 and 10 mM and the pH is between 5 and 7, preferably between 6 and 6.5, most preferably about 6.2.

A serious problem of prior art methods for the isolation of AAT from plasma fractions has been their unsuitability for scaling up to large-scale/commercial isolation. It has now been found that methods comprising two metal chelate affinity chromatography steps can achieve a high yield and high purity preparation of AAT from solutions comprising plasma or plasma fractions without the need for further processing steps such as diafiltration or PEG precipitation. Thus the methods of the invention are capable of being utilised on a large/commercial-scale and being economically viable at that scale.

By "large-scale" it is meant that isolation is achievable from volumes of starting sample in the order of thousands of litres. Viewed alternatively, large-scale refers to starting plasma batch sizes of at least 1000 litres, more preferably at least 3000 litres and most preferably at least 6000 litres.

Previously preferred embodiments of the invention apply *mutatis mutandis* to this aspect of the invention. The skilled man would be able to apply the previously discussed embodiments to large-scale production without undue burden.

The basic methods described above result in AAT of significant purity and activity. However, the direct product of these basic methods of the invention can be subjected to procedures to purify it further and/or concentrate the preparation. The skilled man would know of and be able to apply suitable procedures or devise alternatives. Examples of suitable procedures include, but are not limited to, diafiltration, ultrafiltration, flow through chromatography, further metal chelate chromatography, hydroxyapatite chromatography, and dedicated virus inactivation/reduction procedures.

If the AAT is destined for pharmaceutical use, the isolated and/or purified AAT may need to undergo further processing to remove any biological or chemical contaminants that may remain in the sample. Such procedures are well known in the art and the skilled man would be able to apply his common general knowledge and perform routine testing to enable him to formulate the isolated/purified AAT to be suitable for pharmaceutical use.

Diafiltration may be used to adjust the salt concentration or pH to be suitable for pharmaceutical use.

Biological contaminants such as viruses or prions can be inactivated and/or removed by known virus filtration techniques, by known chemical disinfection (viral inactivation) techniques and/or by known pasteurisation or heat treatment techniques. For example, virus inactivation of a solution containing AAT is possible using solvent detergent treatment as outlined in EP-A 0131740, providing the AAT is treated at a pH which does not lead to AAT inactivation, for example a pH of at least 6. It is also possible to filter the AAT produced by the methods described herein through one or more suitable virus filters, for example filters with pore sizes of about 20 nm, and thus theoretically ensure removal of potentially pathogenic viruses.

If solvent detergent (SD) treatment is used to inactivate viruses a further step may be included in the method to remove the solvent detergent reagents. The skilled man would be familiar with such methods. By way of example, anion exchange chromatography may be used. A suitable anion exchange chromatography step would be the same as those discussed herein. However, any column where either the SD or the protein of interest are separated may be used.

If pasteurisation or heat treatment is used for virus inactivation, the use of stabilisers is contemplated. Stabilisers would include, but are not limited to, sugars, sugar alcohols, ascorbic acid and amino acids. Methods to remove stabilisers, if necessary, are well known in the art.

The particular order of the above mentioned procedures is not considered important, however particular orders may be more advantageous than others in terms of expediency and cost. For instance, it may be preferable to perform pasteurisation with stabilisers or perform a chemical disinfection step prior to a filtration or dialysis step that could be designed to remove the stabilisers or disinfection agent. Conveniently the SD treatment step may be performed in between two of the steps of the basic methods of the invention. Most conveniently a solvent detergent treatment step will occur prior to a step wherein AAT is retained on the chromatography substrate thus allowing the solvent detergent reagents to be removed from the AAT in the flow through or in one or more washing steps. For example, in the first method of the invention, solvent-detergent treatment can be carried out after step (d), and then the reagents can be removed in a further purification step (e), for example an anion exchange chromatography step. However, if SD treatment is performed after a step wherein AAT is retained on the chromatography substrate a further step may be required to remove the SD from the AAT product. The skilled man would be familiar with such methods.

The skilled man would be aware of the advantages and disadvantages of performing a virus inactivation treatment at a particular stage of the methods of the invention. For instance, performing a virus inactivation treatment early in the process ensures that more proteins in the starting material are virus inactivated and so other virus inactivated proteins can be obtained easily using the methods of the invention. However, once a virus inactivation step has been carried out, the downstream steps should be performed in virus secure areas thus reducing the convenience of the process. Furthermore, if a virus inactivation step is carried out early in the process, there is risk that reinfection may occur during the remaining process steps. Accordingly, the skilled man would be able to perform the virus inactivation treatment at a point in the methods of the invention that best suits his needs.

Blood products, including AAT, for use as pharmaceuticals will necessarily undergo at least two viral inactivation/reduction steps.

The AAT produced according to the methods of the invention may be subsequently formulated for clinical use. In such a formulation of AAT, AAT should be substantially free of chemical and biological contaminants, to the extent that the levels in the formulation would not be considered harmful to a patient. Ideally, the levels of any contaminants will be substantially lower than the minimum levels required by Regulatory bodies in relation to pharmaceuticals.

By "biological contaminants" it is meant biological entities capable of inducing pathologies in a patient. Such entities include, but are not limited to, viruses, prions, bacteria, fungi, spores, and cells.

By "chemical contaminants" it is meant molecules that would induce adverse reactions if administered to patients.

Formulations of AAT suitable for pharmaceutical applications may comprise one or more pharmaceutically acceptable excipients. Preferably AAT is formulated as a solution, for example in a form suitable for parenteral administration, particularly intravenous administration, or in a form suitable for administration by inhalation. AAT suitable for pharmaceutical applications may also be in lyophilised form which requires dissolution in a pharmaceutically acceptable diluent prior to administration.

In a still further aspect the invention provides products obtained by any and all methods of the invention hereinbefore described.

As discussed above isolation of AAT is the objective of the invention. The methods of the invention inevitably involve the separation of AAT from the other component(s) of the starting material, in particular albumin. These other components may be contaminants which are to be disposed of as a waste product, or they may be useful molecules that could be isolated and purified if required. Without undue burden the skilled man would be able to assay the components retained on a substrate and/or present in the flow through when AAT is retained and identify other components that could be isolated. Once identified the skilled man would easily adapt the method of the invention to isolate these components in useful forms if desired.

BRIEF DESCRIPTION OF THE DRAWINGS

As shown in FIG. 1, if A+1 supernatant is used as the starting material in the second method of the invention and anion exchange chromatography (e.g. on Capto Q® Sepharose®) is used in step (a1), conditions may be selected in which AAT, haptoglobin and AAG bind to the chromatography substrate whilst most of the albumin does not. Elution of AAT and haptoglobin and retention of AAG can be achieved with a buffer containing 20 mM phosphate and 170 mM NaCl at pH 6.2. AAG can then be isolated from the chromatography substrate with a buffer containing 20 mM phosphate and 500 mM NaCl at pH 6.2.

The haptoglobin can then be separated from the AAT in step (b1), as the haptoglobin will bind to the metal chelate chromatography substrate whilst the AAT does not. After the AAT has been washed off the substrate, the haptoglobin may be eluted using a buffer with a higher concentration of imidazole.

Solvent detergent treatment can be carried out on the product of the first metal chelate chromatography step. In the second metal chelate chromatography step (step (d1)), the AAT binds to the substrate and any residual albumin, together with the solvent detergent reagents, can be removed by washing before the AAT is eluted.

Figure 1:
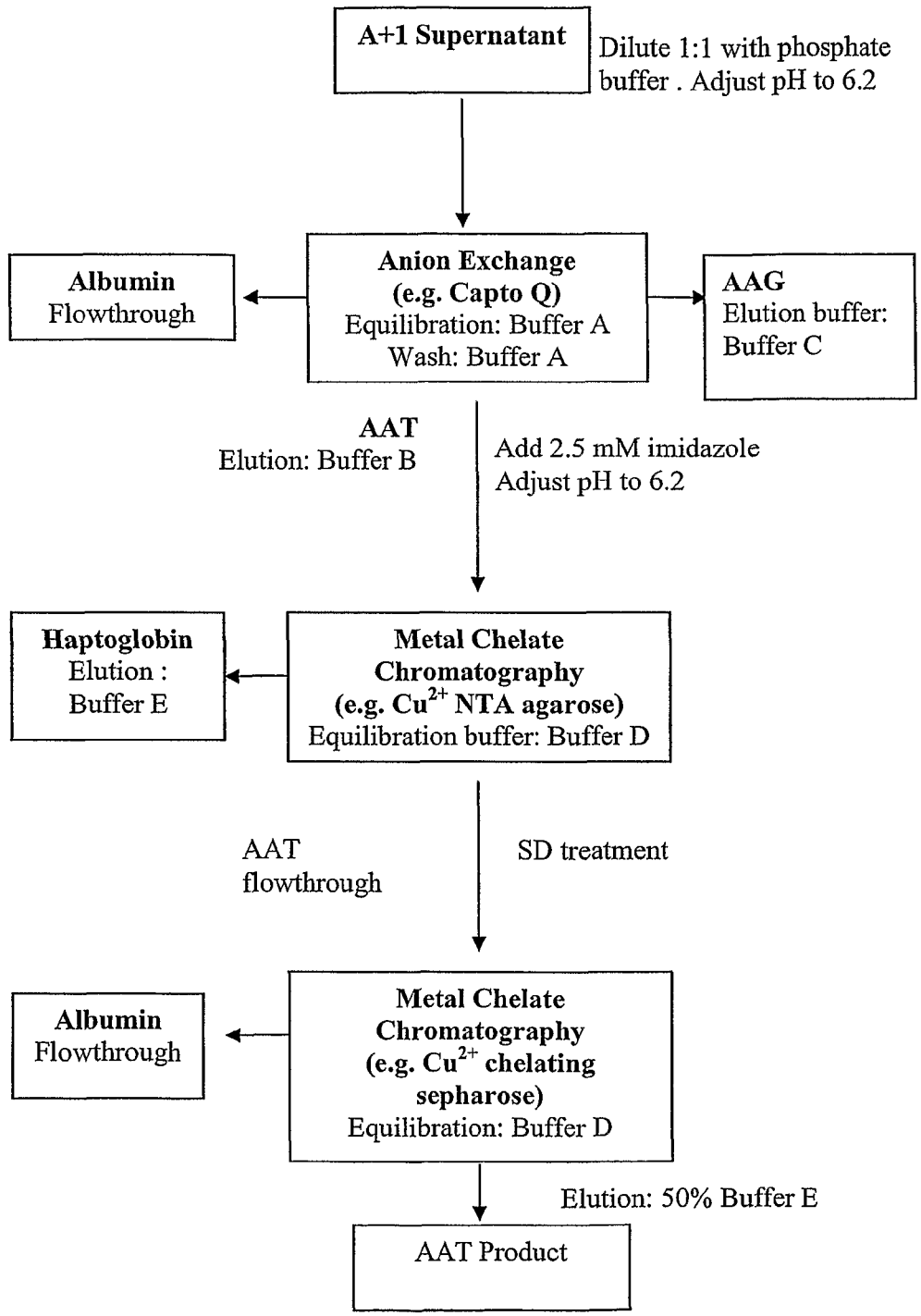
FIG. 1 shows a flowchart depicting a preferred embodiment of the second method of the invention. Buffers A to E are described in Example 2.
Figure 2:
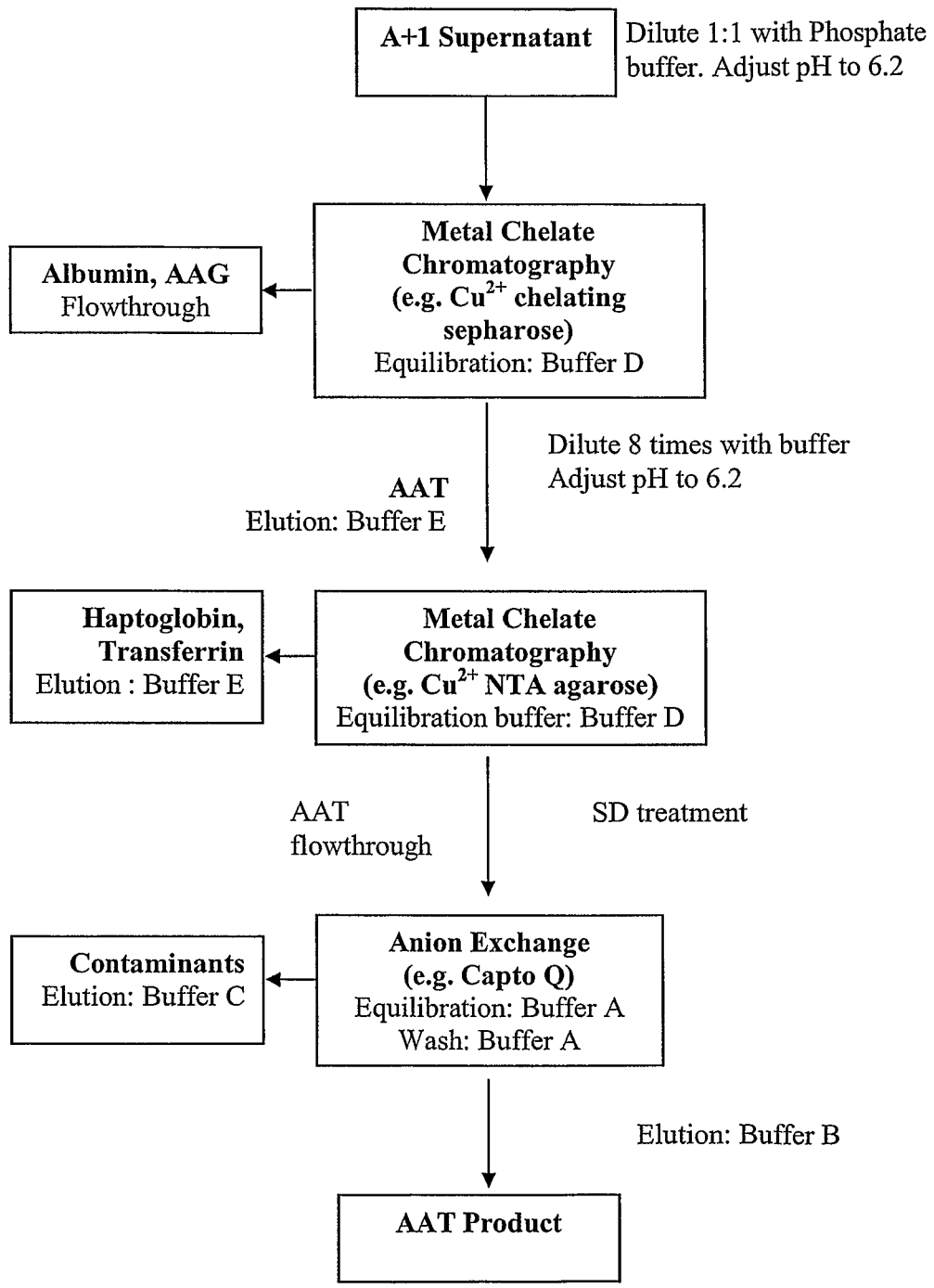
FIG. 2 shows a flowchart depicting a preferred embodiment of the first method of the invention. Buffers A to E are described in Example 2.

FIG. 2 illustrates a preferred embodiment of the first method of the invention. Again, A+1 supernatant is the starting material. This is loaded onto the first metal chelate chromatography substrate under conditions wherein the AAT binds but albumin and AAG do not. The albumin and the AAG may be removed by washing before the AAT is eluted from the substrate by increasing the salt concentration in the buffer.

The AAT is then loaded onto a second metal chelate chromatography substrate under conditions in which the AAT does not bind to the substrate but haptoglobin and transferrin do. The AAT is washed off the substrate, and then the haptoglobin and transferrin can be eluted by increasing the imidazole content in the buffer.

Solvent detergent treatment can be carried out on the product of the second metal chelate chromatography step. In a final anion exchange chromatography step (step (e)), the AAT binds to the substrate and any residual albumin, together with the solvent detergent reagents, can be removed by washing before the AAT is eluted. Other contaminants, for example low molecular weight proteins, may also be removed by washing or by selective elution.

Figure 3:
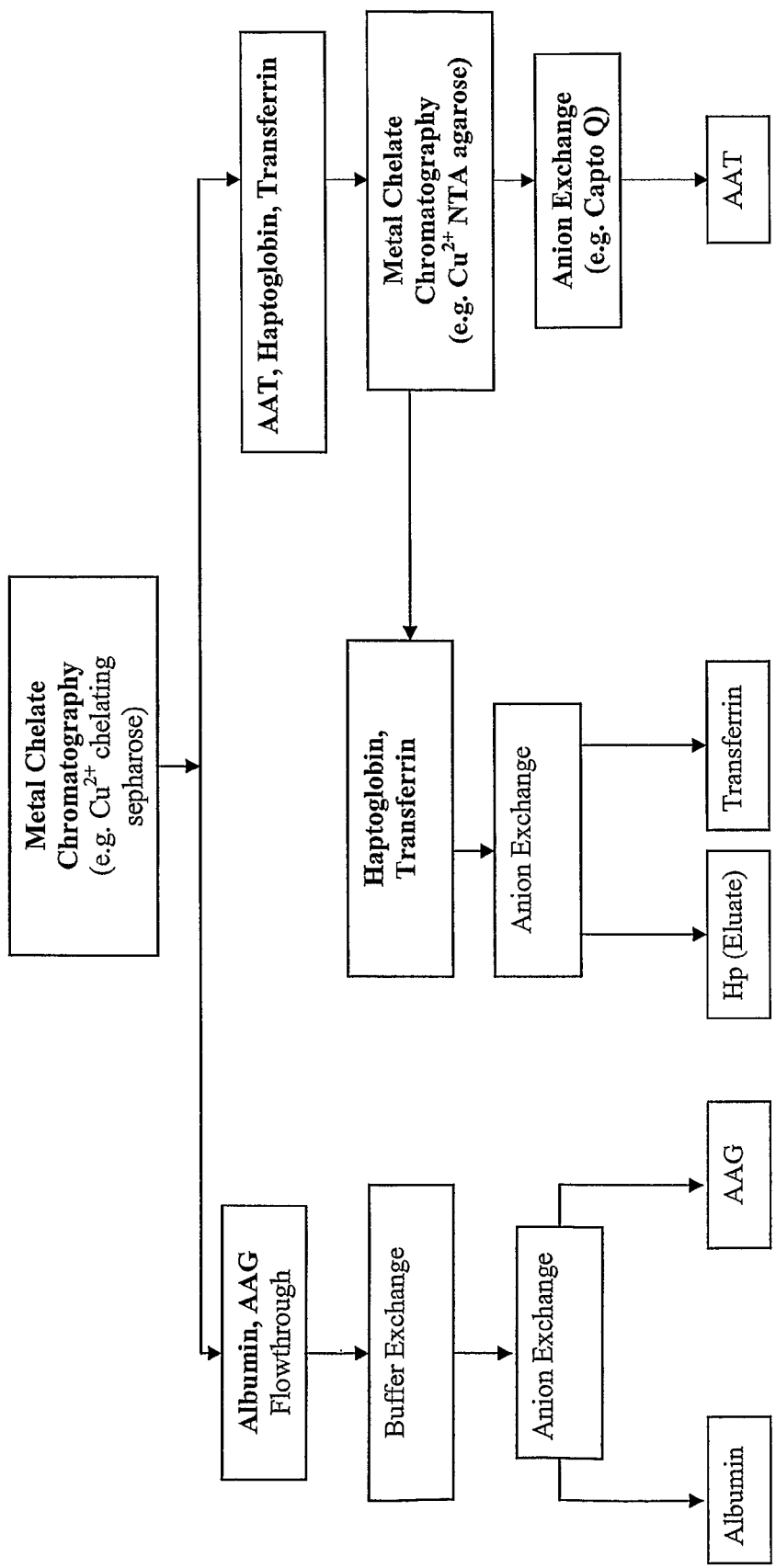
FIG. 3 shows a flowchart depicting the further isolation of albumin, AAG, haptoglobin and transferrin alongside the isolation of AAT according to a preferred embodiment of the first method of the invention.

FIG. 3 elaborates further a preferred embodiment of the first method of the invention in which A+1 supernatant is the starting material and $Cu^{2+}$ charged iminodiacetic acid linked agarose is used as the first chromatography step (step (a)). As can be seen, this method of the invention can be used to isolate albumin, AAG, haptoglobin, and transferrin form the A+1 supernatant in addition to AAT The first chromatography step with $Cu^{2+}$ charged iminodiacetic acid linked agarose retains AAT, haptoglobin and transferrin whist albumin and AAG flow through. The flow though can be collected, and albumin and AAG may be separated by anion exchange chromatography (the albumin will flow through whilst the AAG binds). The AAT, haptoglobin and transferrin retained on the $Cu^{2+}$ charged iminodiacetic acid linked agarose are eluted and loaded onto $Cu^{2+}$ charged NTA linked agarose substrate (step (b)). This allows AAT to flow through and haptoglobin and transferrin to be retained. The AAT flow through may be further purified if required, for example by anion exchange chromatography to remove residual albumin. The retained haptoglobin and transferrin can subsequently be eluted and separated by anion exchange as haptoglobin readily binds an anion exchange substrates but transferrin does not.

Figure 4:
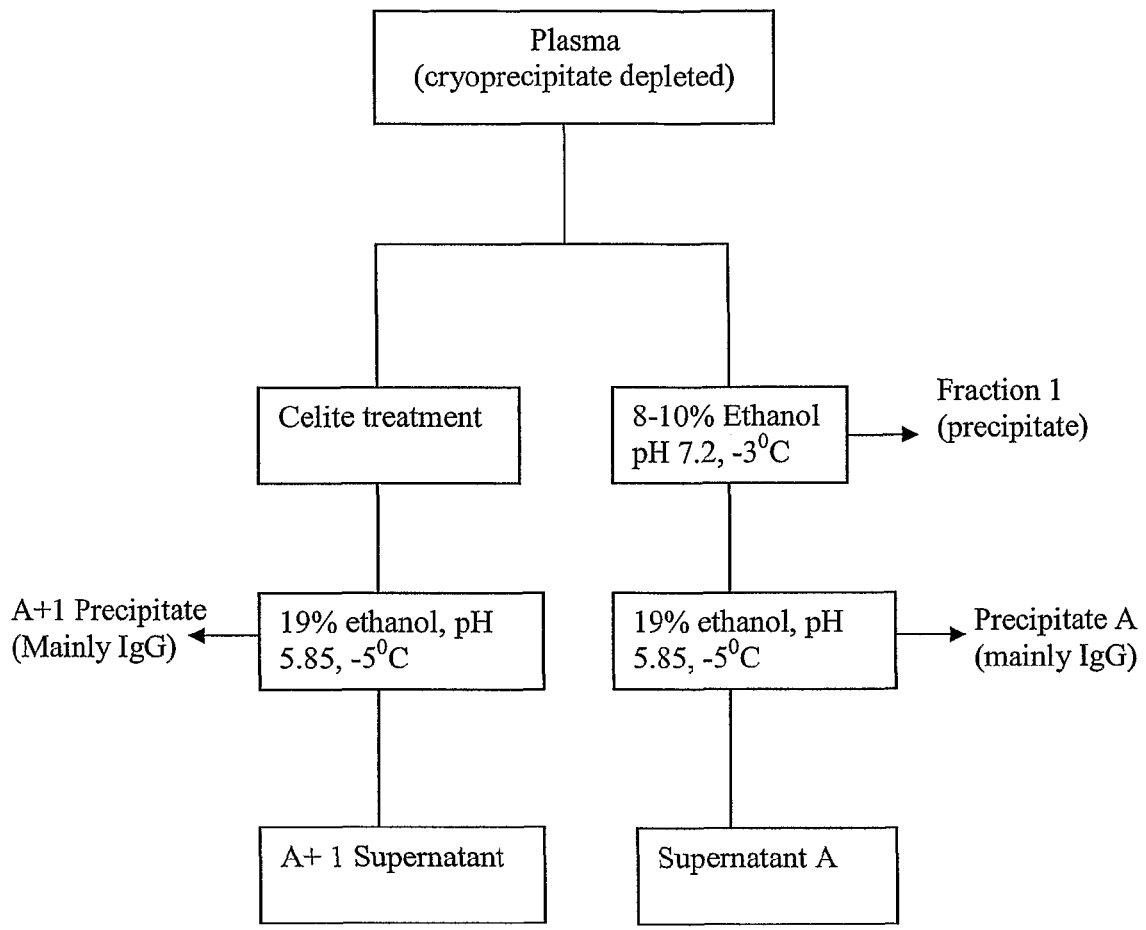
FIG. 4 shows the plasma fraction process which provides the preferred starting material for the methods of the invention (A+1 Supernatant).

FIG. 4 shows the plasma fractionation process which leads to the preferred starting material of the invention (A+1 supernatant) and compares it with the Kistler and Nitschmann process (shown on the right hand side). The A+1 precipitate includes fraction 1 and precipitate A of the Kistler and Nitschmann process.

Any and all combinations of preferred features discussed herein are encompassed by the invention even if not explicitly disclosed. As used herein, the term "comprising" includes the terms "consisting essentially of" and "consisting of".

The invention will be further described with reference to the following non-limiting Examples.

EXAMPLE 1

Preparation of Supernatant A+1

Plasma was subjected to a controlled thaw at –0.5° C. to 2° C. during which some of the proteins precipitated. The supernatant was collected, treated with celite and then filtered to remove other unwanted proteins. The resulting supernatant was adjusted to a pH of 5.85 with acetate buffer and 17-21% ethanol v/v was added. The temperature was controlled during the ensuing precipitation at between –4° C. and –6° C. These conditions are similar to those used in the second stage of the Kistler and Nitschmann process (ibid) and so the precipitate includes Fraction 1 and precipitate A of that process. The precipitate is referred to as A+1 and the supernatant thereof is used as the starting material in the following Examples.

EXAMPLE 2

Buffer Solutions

Buffer A: 20 mM phosphate buffer containing 30 mM NaCl, pH 6.2 (phosphate buffer is made by mixing 20 mM $Na_2HPO_4$ and 20 mM $NaH_2PO_4$ in a volumetric ratio of about 1:4 respectively)
Buffer B: 20 mM phosphate containing 170 mM NaCl, pH 6.2
Buffer C: 20 mM phosphate containing 500 mM NaCl, pH 6.2
Buffer D: 20 mM phosphate containing 30 mM NaCl, 2.5 mM imidazole, pH 6.2
Buffer E: 20 mM imidazole pH 8.

EXAMPLE 3

Isolation of AAT Using Anion Exchange as the First Step (Second Method of the Invention)

A+1 supernatant was diluted 1:1 with 10 mM $NaH_2PO_4$ containing 10 mM NaOH, pH 11. Diluting the A+1 supernatant reduced the concentration of ethanol which is known to damage AAT over time. The pH of the resulting solution was between 6 and 7 and the conductivity was less than 7 mS/cm. Just prior to loading onto the Capto Q sepharose column the pH was reduced to between 5.5 and 6.5 with dilute acetic acid. This ensured that most of the albumin flowed through the column whilst AAT was retained.

The column was equilibrated with Buffer A. This buffer has conductivity similar to the A+1 supernatant diluted 1:1 with buffer containing 10 mM $NaH_2PO_4$ and 10 mM NaOH.

The AAT fraction was then eluted with Buffer B. Some tightly bound molecules such as alpha-1 acid glycoprotein (AAG) remained on the column at this concentration and were eluted with a higher NaCl concentration (i.e. Buffer C).

2.5 mM of imidazole was added to the AAT fraction eluted from the Capto Q column. The imidazole treated AAT fraction was then loaded onto a HisTrap column stripped of its nickel ions and re-charged with divalent copper cations. At this imidazole concentration and using this type of chelating solid support, some of the contaminants bound to the solid support, however, AAT did not. The flow through also contained residual albumin that was bound by the Capto Q column in the previous step rather than flowing through.

To reduce the viral load of the AAT fraction, a polysorbate 20/tri-n-butyl phosphate (TNBP) mixture was added according to EP-A 0131740. The solvent detergent (SD) treated AAT fraction was then loaded onto a chelating sepharose solid support (iminodiacetic acid chelating ligand) charged with copper. Under the conditions of the load (2.5 mM imidazole in 20 mM phosphate buffer containing 30 mM NaCl, pH 6.2) the AAT was bound by the solid support whilst the contaminants, mostly albumin, were not. The AAT was then eluted with 10 mM imidazole solution.

EXAMPLE 4

Isolation of AAT Using Chelating Sepharose as the First Step (First Method of the Invention)

A+1 supernatant was diluted 1:1 with 10 mM $NaH_2PO_4$ containing 10 mM NaOH, pH 11. The pH of the resulting solution was between 6 and 7 and the conductivity was less than 7 mS/cm. Just prior to loading onto the chelating sepharose column the pH was reduced to between 6.0 and 6.5 with dilute acetic acid. This ensured that most of the albumin and other proteins flowed through the column whilst AAT was retained.

The chelating sepharose used comprised iminodiacetic acid as the chelating ligand and was charged with divalent copper cations. 2.5 mM Imidazole was added to the 1:1 diluted A+1 supernatant and pH was adjusted to 6.2. This was then loaded onto the copper chelating sepharose column and equilibrated with Buffer D. Under these conditions more than 90% of total protein of the A+1 supernatant flowed through the solid support and less than 0.5% of albumin was bound. The flow through was mostly albumin but it also contained some of the haptoglobin dimer that was present in the starting material.

The bound proteins, including AAT, were eluted with 20 mM imidazole solution. The eluate was then diluted 8 times so that the imidazole concentration was 2.5 mM. This protein mixture was then loaded onto a stripped HisTrap column charged with copper. Under these loading conditions, the AAT fraction flowed through the column whilst the contaminants, mainly haptoglobin and transferrin, were bound. The AAT fraction obtained at this stage was at least 80% pure by SDS-PAGE, with the main contaminants being albumin, and low molecular weight proteins, possibly fragments or apolipoprotein A.

Polysorbate 20/TnBP (SD) was added to the AAT solution according to EP-A 0131740. The SD treated AAT was then loaded onto a Capto Q anion exchange column and equilibrated with Buffer A. Under these loading conditions, the SD flowed through whilst the proteins were bound.

The AAT was eluted with Buffer B. The bound proteins were eluted using a higher salt concentration (Buffer C). The AAT obtained at this stage was at least 90% pure and 95% active by elastase binding activity.

The invention claimed is:

1. A method for the isolation of alpha-1-antitrypsin (AAT) from a solution containing albumin and AAT, comprising the steps of:
   (a) optionally removing albumin from the solution,
   (b) loading the solution onto a first metal chelate chromatography substrate, wherein the chelating ligand of said substrate is iminodiacetic acid, under conditions whereby AAT is bound and retained on the first metal chelate chromatography substrate and albumin, if present, is not retained on the first metal chelate chromatography substrate;
   (c) selectively eluting AAT from the first metal chelate chromatography substrate;
   (d) loading the AAT eluate obtained from step (c) onto a second metal chelate chromatography substrate, wherein the chelating ligand of said substrate is nitrilotriacetic acid (NTA), under conditions whereby AAT remains in a flow through solution and is not bound and retained on the second metal chelate chromatography substrate;
   (e) collecting the flow through solution containing AAT; and
   (f) optionally carrying out one or more further chromatographic purification steps on the AAT solution; thereby providing an isolated AAT.

2. The method according to claim 1, further comprising an additional chromatographic purification step between steps (c) and (d).

3. The method according to claim 1 or claim 2, wherein the further chromatographic purification step and/or the additional chromatographic purification step is an anion exchange chromatography step.

4. A method for the isolation of AAT from a solution containing albumin and AAT, comprising the steps of:
   (a) removing albumin from the solution to provide an albumin depleted solution;
   (b) loading the albumin depleted solution onto a first metal chelate chromatography substrate, wherein the chelating ligand of said substrate is nitrilotriacetic acid, under conditions whereby AAT remains in a flow through solution and is not bound and retained on the first metal chelate chromatography substrate;
   (c) collecting the flow through solution containing AAT;
   (d) loading the solution obtained from step (c) onto a second metal chelate chromatography substrate, wherein the chelating ligand of said substrate is iminodiacetic acid, under conditions whereby AAT is bound and retained on the second metal chelate chromatography substrate; and
   (e) selectively eluting AAT from the second metal chelate chromatography substrate; thereby providing an isolated AAT.

5. The method according to claim 4 wherein the step of removing albumin from the solution is an anion exchange chromatography step.

6. The method according to claims 1 or 4, wherein the metal ion of the metal chelate chromatography substrate is selected from the group consisting of $Zn^{2+}$, $Ni^{2+}$, $Cu^{2+}$, $Co^{2+}$, and $Fe^{2+}$.

7. The method according to claims 1 or 4, wherein the metal chelate chromatography substrate on which AAT is to be retained is iminodiacetic acid agarose charged with $Cu^{2+}$ ions.

8. The method according to claims 1 or 4, wherein the metal chelate chromatography substrate used in the metal chelate chromatography step in which AAT remains in solution is NTA agarose charged with $Cu^{2+}$ ions.

9. The method according to claims 1 or 4, wherein the solution containing albumin and AAT is plasma or a plasma fraction.

10. The method according to claim 9 wherein the plasma or the plasma fraction is human plasma or a human plasma fraction.

11. The method according to claims 1 or 4, wherein the solution containing albumin and AAT comprises mainly AAT, alpha-1-acid glycoprotein, transferrin, haptoglobin, alpha-2 HS glycoprotein, haemopexin, alpha-2 macroglobulin, alpha-1 antichymotrypsin and albumin.

12. The method according to claims 1 or 4, further comprising at least one concentration and/or purification step.

13. The method according to claim 12, wherein the concentration and/or purification step is selected from the group consisting of diafiltration, ultrafiltration, flow through chromatography, further metal chelate chromatography and hydroxyapatite chromatography.

14. The method according to claims 1 or 4, further comprising at least one contaminant removal step.

15. The method according to claim 14, wherein the contaminant removal step is a virus inactivation or removal step.

16. The method according to claim 15, wherein the virus inactivation or removal step comprises solvent detergent treatment and/or virus filtration.

17. The method according to claim 16, wherein the solvent detergent treatment step occurs prior to a step wherein AAT is retained on a chromatography substrate.

18. The method according to claims 1 or 4, further comprising formulating the isolated AAT for pharmaceutical use.

19. The method according to claim 1 or 4, wherein the metal cation of the first and second metal chelate chromatography substrate is the same.

* * * * *